United States Patent [19]

Chodkowski, deceased

[11] Patent Number: 4,664,629

[45] Date of Patent: May 12, 1987

[54] DENTAL COMPOSITION MIXTURE

[75] Inventor: Michael R. Chodkowski, deceased, late of Milford, Del., by Jean C. Chodkowski, administrator

[73] Assignee: Dentsply Research & Development Corp., Milford, Del.

[21] Appl. No.: 726,073

[22] Filed: Apr. 22, 1985

Related U.S. Application Data

[63] Continuation of Ser. No. 508,368, Jun. 27, 1983, abandoned.

[51] Int. Cl.$^4$ .............................................. C22C 5/08
[52] U.S. Cl. ................................. 433/228.1; 75/255; 420/503; 420/504; 420/527
[58] Field of Search ............... 420/526, 527, 502, 503, 420/504; 75/251, 255, 0.5 R; 433/226, 228

[56] References Cited

U.S. PATENT DOCUMENTS

| | | | |
|---|---|---|---|
| 3,871,876 | 3/1975 | Asgar et al. | 420/527 |
| 3,975,192 | 8/1976 | Simpson | 420/502 |
| 3,985,558 | 10/1976 | Simpson | 420/527 |
| 3,997,329 | 12/1976 | Aliotta et al. | 75/0.5 R |
| 3,997,330 | 12/1976 | Aliotta et al. | 75/0.5 R |
| 4,080,199 | 3/1978 | Sung et al. | 420/587 |
| 4,226,622 | 10/1980 | Aliotta | 75/251 |
| 4,234,339 | 11/1980 | Aliotta et al. | 75/255 |
| 4,235,631 | 11/1980 | Aliotta et al. | 75/251 |
| 4,374,085 | 2/1983 | Asgar et al. | 420/470 |

FOREIGN PATENT DOCUMENTS

| | | | |
|---|---|---|---|
| 33628 | 8/1981 | European Pat. Off. | 75/255 |
| 2076854 | 12/1980 | United Kingdom . | |

*Primary Examiner*—Christopher W. Brody
*Attorney, Agent, or Firm*—Woodcock Washburn Kurtz Mackiewicz & Norris

[57] ABSTRACT

By the present invention a dental alloy mixture is provided that is a combination of 20 to 70 percent by weight of cut alloy comprising silver, tin, and copper, with the copper present in an amount of 0 to 30 percent by weight of the cut alloy; and 30 to 80 percent by weight of spherical alloy comprising silver and cooper.

7 Claims, No Drawings

DENTAL COMPOSITION MIXTURE

This is a continuation of application Ser. No. 508,368 filed June 27, 1983 now abandoned.

This invention relates to dental composition mixtures of cut and spherical alloys, especially to those containing silver, tin, or copper, and those titrated with mercury.

Dental amalgams are produced by intimately combining mercury with dental amalgam alloys. Conventional alloys have a major proportion of silver and a lesser proportion of tin and optionally contain other ingredients such as copper, zinc, and palladium. Upon reaction with mercury using known dental clinical techniques, a plastic mass is produced which quickly sets into a hard, rigid body. While the mass is plastic it may be packed into a surgically prepared tooth, restoring its anatomy and function.

The products of the amalgamation reaction are believed to be a silver-mercury reaction product ($Ag_2Hg_3$) and a tin-mercury reaction product ($Sn_{7-8}Hg$), referred to in the art as gamma-1 and gamma-2, respectively. It has been recognized that the presence of gamma-2 in dental amalgams is a source of corrosion in a saline environment. It is believed that the corrosion process probably releases mercury as a reaction product, resulting in the formation of additional voids and porosities. These may extend well below the surface since the gamma-2 phase in dental amalgam is interconnected. The excess mercury, voids, and porosities serve to weaken the dental amalgam especially at the margins which are the interfaces between the restoration and tooth. As a consequence of normal occlusion, stresses generated at a weakened margin may destroy its integrity, allowing leakage of oral fluids and bacteria, thereby promoting secondary decay.

Regardless of whether the aforementioned explanation of the corrosion process due to the presence of gamma-2 is correct (and the present invention is not necessarily limited thereto), it has been found that corrosion can be reduced by techniques which minimize, inhibit, or eliminate gamma-2 from dental amalgam compositions.

U.S. Pat. No. 3,997,329 teaches the expediency of using a mixture of spheroid and irregularly shaped particles which when amalgamated with mercury exhibit enhanced dental properties. The aforesaid patent which is incorporated herein by reference describes in some detail the characteristics of spheroidal particles and the characteristics of irregular shaped particles including the lathe-cut material which is particularly referred in the instant invention of the present application.

It is also known to use palladium and dental alloys to obtain the advantages thereof. An example of this is British Pat. No. 2,076,854. In the past, a palladium containing alloy has been sold by the assignee of the present application. The alloy contained 49.5 plus or minus 5 percent silver (Ag), 30.0 plus or minus 5 percent tin (Sn), 20.0 plus or minus 5 percent copper (Cu), and 0.5 percent palladium (Pd).

OBJECTS OF THE INVENTION

It is a general object of this invention to provide dental amalgam compositions which cope with the aforementioned problems of other amalgams.

It is a specific object to provide high-copper-content dental amalgamable alloys which are substantially free of mercury prior to amalgamation and which can be readily amalgamated without undue risks to personnel resulting from excessive mercury exposure.

It is another specific object to provide new dental amalgam compositions which upon amalgamation with mercury limit the gamma-2 phase which form and which provide enhanced physical, handling, and electrochemical properties.

It is another specific object to provide dental amalgam compositions which upon amalgamation with mercury substantially immediately inhibit gamma-2 formation so as to be substantially free of the gamma-2 phase and yet are competitive in cost with other amalgam compositions.

It is another specific object to provide dental amalgam compositions having improved properties upon amalgamation without unduly increasing the amounts of mercury required in the preparation thereof.

It is another specific object to provide a dental amalgam composition having condensing, working, carving, and adapting qualities superior to spheroidal amalgams or conventional irregularly-shaped microcut amalgams.

It is still another specific object to provide a dental amalgam which is substantially free of any tendency to ride up along walls of a cavity and packs firmly.

These and other objects will become apparent as the detailed description proceeds.

DESCRIPTION OF THE INVENTION

The present invention in its preferred embodiment is a new and improved dental amalgam composition that is a uniform mixture of two different alloy powders. One of the alloy powders is a cut alloy and the other alloy powder is a spherical alloy. These distinctly different alloy powders are preferably combined in amounts of 20 to 70 percent cut alloy with 30 to 80 percent spherical alloy by weight of the two powders, more preferably 30 to 50 percent cut alloy with 50 to 70 percent spherical alloy, and most preferably 35 to 45 percent cut alloy with 55 to 65 percent spherical alloy.

The cut alloy is preferably composed of the following ingredients in the amounts indicated by weight:

| Element | Preferred | More Preferred | Most Preferred |
|---|---|---|---|
| Silver | 40–70% | 52–62% | 54–60% |
| Tin | 37–19% | 34–25% | 32–27% |
| Copper | 30–9% | 15–12% | 14–13% |
| Zinc | 0–2% | 0–1% | 0 |

The percentages above are by weight of the total cut alloy composition.

A spherical alloy component is composed of the following elements in the proportions indicated by weight:

| Element | Preferred | More Preferred | Most Preferred |
|---|---|---|---|
| Silver | 40–70% | 49–60% | 49.2–49.5% |
| Tin | 40–20% | 31–29% | 31–29% |
| Copper | 30–15% | 25–17% | 21–18% |
| Palladium | 0.1–1.5% | 0.2–1.2% | 0.3–1% |

The alloy mixture is preferably amalgamated with 40 to 55 percent mercury by weight of the combined weight of the mercury and alloy mixture, more preferably 45 to 50 percent mercury.

It is particularly important to maintain the copper content of the cut alloy between 9 and 30 percent and of a spherical alloy between 15 and 30 percent to provide sufficient copper content to react with the mercury released and limit the gamma 2 phase.

EXAMPLE I

Fifty-seven grams of silver and 13.8 grams of copper were melted together at 1093° C. in an induction furnace under an atmosphere of carbon monoxide. Twenty-nine and two tenths grams of tin were added to bring the melt temperature to 982° C. The liquid metal was poured into preheated cast iron ingot molds and then allowed to cool to ambient temperature. The resulting ingot slabs were annealed for 24 hours at 350° C. under charcoal cover. A Horizontal Milling Machine cutter containing 22 teeth rotating at 170 rpm at a feed rate of 0.5 inch per minute was used to cut the ingots. The cut alloy was screened to 80 mesh and ball milled in a porcelain mill with porcelain grinding media for 60 minutes at 30 rpm. The resultant powder was screened to −325 mesh and annealed at 100° C. for 11 hours.

A suspension of 450 ounces of the annealed alloy in 4,500 ml. of methanol was treated with hydrochloric acid, slurried and heated until the aqueous methanol was boiled away. The resultant powder was washed by decantation until the wash was at pH7, reslurried and treated with aqueous ammonium hydroxide. The ammonium hydroxide solution was decanted and the alloy washed with water until the wash solution was at pH7. The alloy was dried below 83° C. and screened to −150 mesh. This alloy was referred to as the cut component.

The above product had the following composition: silver-57 percent, tin-29.2 percent, copper-13.8 percent. Excluding any inherent impurities this accounts for 100 percent of the cut powder.

The spherical powder or component was a spherical alloy sold by the L. D. Caulk Company Division of Dentsply International Inc., the assignee of the present patent application, under the tradename Valiant, and had the following composition or assay: silver-49.5 percent, tin-30 percent, copper-20 percent, and palladium-0.5 percent. The cut powder and the spherical powder were combined in a ratio of 60 percent spherical to 40 percent cut by weight by tumble blending.

The mixed alloy composition was triturated with 47.7 percent mercury using a VARI-MIX ® II M mechanical triturating device sold by the L. D. Caulk Division Dentsply International, at speed M2 for thirteen seconds with the following results:

| One-Hour Compressive Strength (208 MPa) | 30,100 PSI |
| 24-Hour Compressive Strength (505 MPa) | 73,200 PSI |
| 24-Hour Dimensional Change | −6 um/cm |
| 7-Day Static Creep | 0.1 percent |
| (EAMES) Work Time | 4 minutes |

The EAMES test is set forth in a publication: EAMES, W. B., and Skinner, EW 1965 International Association for Dental Research Program and Abstracts of Papers, Abstract 94, page 60.

The amalgum of Example I was used to provide a dental restoration and found to give excellent working characteristics and to perform well in the dental operatory. The dental preparation was made for receipt of the restoration amalgum material and the alloy composition was triturated with mercury and placed in a dental cavity preparation. The placed mass of alloy was packed into the dental preparation to substantially fill it and shaped in the conventional manner.

EXAMPLE II

The above procedure was repeated except the compositions of the alloy powders were:

| Cut Component | | Spherical Component | |
|---|---|---|---|
| Silver | 59 | Silver | 49.5 |
| Tin | 29 | Tin | 30 |
| Copper | 11 | Copper | 20 |
| Zinc | 1 | Palladium | 0.5 |

The mixed alloy composition was triturated with 49 percent of mercury in the manner of Example I and the results were:

| One-Hour Compressive Strength (210 MPa) | 30,400 PSI |
| 24-Hour Compressive Strength (492 MPa) | 71,400 PSI |
| 24-Hour Dimensional Change | −3 um/cm |
| 7-Day Static Creep | 0.1 percent |
| (EAMES) Work Time | 5 minutes |

EXAMPLE III

The above procedure was repeated except the compositions of the alloy powders were:

| Cut Alloy | | Spherical Alloy | |
|---|---|---|---|
| Silver | 57.0 | Silver | 49.2 |
| Tin | 29.2 | Tin | 30 |
| Copper | 13.8 | Copper | 20 |
| Zinc | 0 | Palladium | 0.8 |

The mixed alloy composition was triturated with 47.7 percent of mercury in the manner of Example I and the results were

| One-Hour Compressive Strength (207 MPa) | 30,000 PSI |
| 24-Hour Compressive Strength (457 MPa) | 66,200 PSI |
| 24-Hour Dimensional Change | −4 um/cm |
| 7-Day Static Creep | 0.1 percent |
| (EAMES) Work Time | 4 minutes |

While in accordance with the patent statutes what is at present considered to be the preferred embodiment of the invention has been described, it will be obvious to those skilled in the art that numerous changes and modifications may be made therein without departing from the invention, and it is therefore aimed in the appended claims to cover all such equivalent variations as fall within the true spirit and scope of the invention.

It is claimed:

1. A dental alloy mixture for use as a filling for dental preparations after amalgamation consisting essentially of:
    (a) from about 35% to about 45% by weight of said mixture of cut alloy consisting essentially of about 52% to about 62% silver, about 12% to about 15% copper, about 25% to about 34% tin and about 0% to about 1% zinc by weight of said cut alloy; and
    (b) from about 55% to about 65% by weight of said mixture of spherical alloy consisting essentially of about 49% to about 60% silver, about 17% to about 25% copper, about 29% to about 31% tin, and about 0.2% to about 1.2% palladium by weight of said spherical alloy.

2. The dental alloy mixture of claim 1 wherein said cut alloy is present in an amount between about 35% and 40% of said mixture and said spherical alloy is present in an amount between about 60% and 65% of said mixture.

3. The dental alloy mixture of claim 1 wherein said cut component consists essentially of about 54% to about 60% silver, about 13% to about 14% copper, and about 27% to about 32% tin by weight of said cut alloy; and said spherical alloy consists essentially of about 49.2% to about 49.5% silver, about 18% to about 21% copper, about 29% to about 31% tin, and about 0.3% to about 1% palladium by weight of said spherical alloy.

4. The dental alloy mixture of claim 1 amalgamated with about 40% to about 55% of mercury by weight of the combined weight of said mercury and said mixture.

5. The dental alloy mixture of claim 3 triturated with about 45% to about 50% of mercury by weight of the combined weight of said mercury and said mixture.

6. A method of dental restoration comprising providing a dental preparation for receipt of restorative material; triturating a dental alloy mixture in accordance with claim 1, 2, or 3; placing said triturated mass in said dental preparation; and packing said mass in said dental preparation to substantially fill said preparation.

7. The method of claim 6 wherein said trituration is with from about 40% to about 55% of mercury by weight of the combined weight of said mercury and said mixture.

* * * * *